(12) United States Patent
Shameli et al.

(10) Patent No.: US 11,833,013 B2
(45) Date of Patent: Dec. 5, 2023

(54) METHOD FOR TREATING PATULOUS EUSTACHIAN TUBE

(71) Applicant: Acclarent, Inc., Irvine, CA (US)

(72) Inventors: Ehsan Shameli, Irvine, CA (US);
Babak Ebrahimi, Irvine, CA (US);
Itzhak Fang, Irvine, CA (US);
Fatemeh Akbarian, Rancho Palos Verdes, CA (US)

(73) Assignee: Acclarent, Inc., Irvine, CA (US)

( * ) Notice: Subject to any disclaimer, the term of this patent is extended or adjusted under 35 U.S.C. 154(b) by 821 days.

(21) Appl. No.: 16/920,818

(22) Filed: Jul. 6, 2020

(65) Prior Publication Data

US 2021/0045924 A1 Feb. 18, 2021

Related U.S. Application Data

(60) Provisional application No. 62/886,392, filed on Aug. 14, 2019.

(51) Int. Cl.
*A61F 11/20* (2022.01)
*A61B 1/233* (2006.01)
*A61B 17/24* (2006.01)

(52) U.S. Cl.
CPC ............ *A61F 11/202* (2022.01); *A61B 1/233* (2013.01); *A61B 17/24* (2013.01); *A61F 2210/0004* (2013.01); *A61F 2210/0014* (2013.01)

(58) Field of Classification Search
CPC ........ A61F 11/20; A61F 11/202; A61B 1/233; A61B 17/24
See application file for complete search history.

(56) References Cited

U.S. PATENT DOCUMENTS

| | | | |
|---|---|---|---|
| 4,888,017 A | 12/1989 | DeVore et al. | |
| 6,589,286 B1 | 7/2003 | Litner | |
| 8,532,780 B2 | 9/2013 | Ozkul et al. | |
| 8,579,973 B2 | 11/2013 | Avior | |
| 8,961,495 B2 | 2/2015 | Chang et al. | |
| 9,782,297 B2 | 10/2017 | Mandpe | |
| 10,376,416 B2* | 8/2019 | Clifford | A61F 2/2476 |
| 11,311,419 B2* | 4/2022 | Campbell | A61B 17/00234 |
| 2007/0112290 A1 | 5/2007 | Morita | |
| 2013/0274715 A1 | 10/2013 | Chan et al. | |
| 2017/0027724 A1* | 2/2017 | Hossainy | A61F 11/202 |
| 2017/0252089 A1* | 9/2017 | Hester | A61B 18/20 |
| 2021/0045924 A1* | 2/2021 | Shameli | A61B 1/233 |
| 2021/0052318 A1* | 2/2021 | Hester | A61B 18/20 |

(Continued)

*Primary Examiner* — Suzette J Gherbi

(74) *Attorney, Agent, or Firm* — Frost Brown Todd LLP

(57) ABSTRACT

A method of treating a patulous Eustachian tube includes forming a first pocket in a wall of a nasopharynx region proximate to a pharyngeal ostium, inserting a resiliently biased implant within the first pocket, and allowing the resiliently biased implant to expand within the first pocket to thereby urge the Eustachian tube towards a closed state. The wire implant may include a resilient stent or other resilient wire structure. In some versions, a deployment device having a balloon is used to deploy a malleable implant. This deployment device has a malleable implant disposed around the balloon, which is disposed around a guide catheter. The balloon is inflated and expands the malleable implant. The malleable implant retains the expanded shape and urges the Eustachian tube toward a closed state.

20 Claims, 18 Drawing Sheets

(56) References Cited

U.S. PATENT DOCUMENTS

2022/0211546 A1* 7/2022 Campbell .............. A61B 1/233
2023/0190528 A1* 6/2023 Palushi ................ A61F 11/202
                                                                                             623/10

\* cited by examiner

# METHOD FOR TREATING PATULOUS EUSTACHIAN TUBE

PRIORITY

This application claims priority to U.S. Provisional Pat. App. No. 62/886,392, entitled "Method for Treating Patulous Eustachian Tube," filed Aug. 14, 2019, the disclosure of which is incorporated by reference herein in its entirety.

BACKGROUND

Referring to FIG. 1, the ear (10) is divided into three parts: an external ear (12), a middle ear (14) and an inner ear (16). The external ear (12) consists of an auricle (18) and ear canal (20) that gather sound and direct it toward a tympanic membrane (22) (also referred to as the eardrum) located at an inner end (24) of the ear canal (20). The middle ear (14) lies between the external and inner ears (12, 16) and is connected to the back of the throat by a Eustachian tube (ET) (26), which serves as a pressure equalizing valve between the ear (10) and the throat (32). The ET (26) terminates in a pharyngeal ostium (28) in the nasopharynx region (30) of the throat (32). In addition to the eardrum (22), the middle ear (14) also consists of three small ear bones (ossicles): the malleus (34) (hammer), incus (36) (anvil) and stapes (38) (stirrup). These bones (34, 36, 38) transmit sound vibrations to the inner ear (16) and thereby act as a transformer, converting sound vibrations in the canal (20) of the external ear (12) into fluid waves in the inner ear (16). These fluid waves stimulate several nerve endings (41) that, in turn, transmit sound energy to the brain where it is interpreted.

The ET (26) is a narrow, one-and-a-half inch long channel connecting the middle ear (14) with the nasopharynx (30), the upper throat area just above the palate, in back of the nose. A narrowed region known as the isthmus (29) of the ET (26) provides a transition between the remainder of the ET (26) and the middle ear (14). The isthmus (29) is the narrowest part of the ET (26) at the junction of the bony and cartilaginous parts of the ET (26) (i.e., where the bony canal meets the cartilaginous tube). The isthmus (29) thus has a reduced inner diameter compared to the remaining portion of the ET (26) that extends between the isthmus (29) and the pharyngeal ostium (28); and provides a density that is substantially greater than the density of the tissue of the remaining portion of the ET (26) that extends between the isthmus (29) and the pharyngeal ostium (28).

The ET (26) functions as a pressure equalizing valve for the middle ear (14), which is normally filled with air. When functioning properly, the ET (26) opens for a fraction of a second periodically (e.g., about once every three minutes) in response to swallowing or yawning. In so doing, it allows air into the middle ear (14) from the throat (32), to replace air that has been absorbed by the middle ear lining (mucous membrane) or to equalize pressure changes occurring on altitude changes. Anything that interferes with this periodic opening and closing of the ET (26) may result in hearing impairment or other ear symptoms.

Obstruction or blockage of the ET (26) results in a negative middle ear (14) pressure, with retraction (sucking in) of the eardrum (22). In adults, this may be accompanied by some ear discomfort, a fullness or pressure feeling and may result in a mild hearing impairment and head noise (tinnitus). There may be no symptoms in children. If the obstruction is prolonged, fluid may be drawn from the mucous membrane of the middle ear (14), creating a condition referred to as serous otitis media (fluid in the middle ear). This may occur frequently in children in connection with an upper respiratory infection and account for hearing impairment associated with this condition.

In some cases, rather than being restricted or blocked, the ET (26) may fail to close properly. The ET (26) may take an inordinately prolonged amount of time to close after being opened, such that the ET (26) substantially remains in a patulous state. This physical disorder is called Patent Eustachian Tube or PET. When PET occurs, the patient experiences autophony, the hearing of self-generated sounds. These self-generated sounds are one's own breathing, voice, and heartbeat. These self-generated sounds vibrate directly onto the ear drum (22) and can cause significant discomfort for the patients. PET is a form of Eustachian Tube Dysfunction (ETD). One form of treatment of PET includes creating a pocket in the tissue surrounding the ET and filling the pocket with either a cartilage graft or collagen-calcium phosphate paste. This operation collapses the ET (26) wall inwardly and results in the closure of the ET (26). However, the cartilage graft or collagen-calcium phosphate may dissolve into tissue within one to three years and the surgery may need to be repeated. It may therefore be desirable to provide a more permanent treatment of PET.

While a variety of surgical methods have been used, it is believed that not one, prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
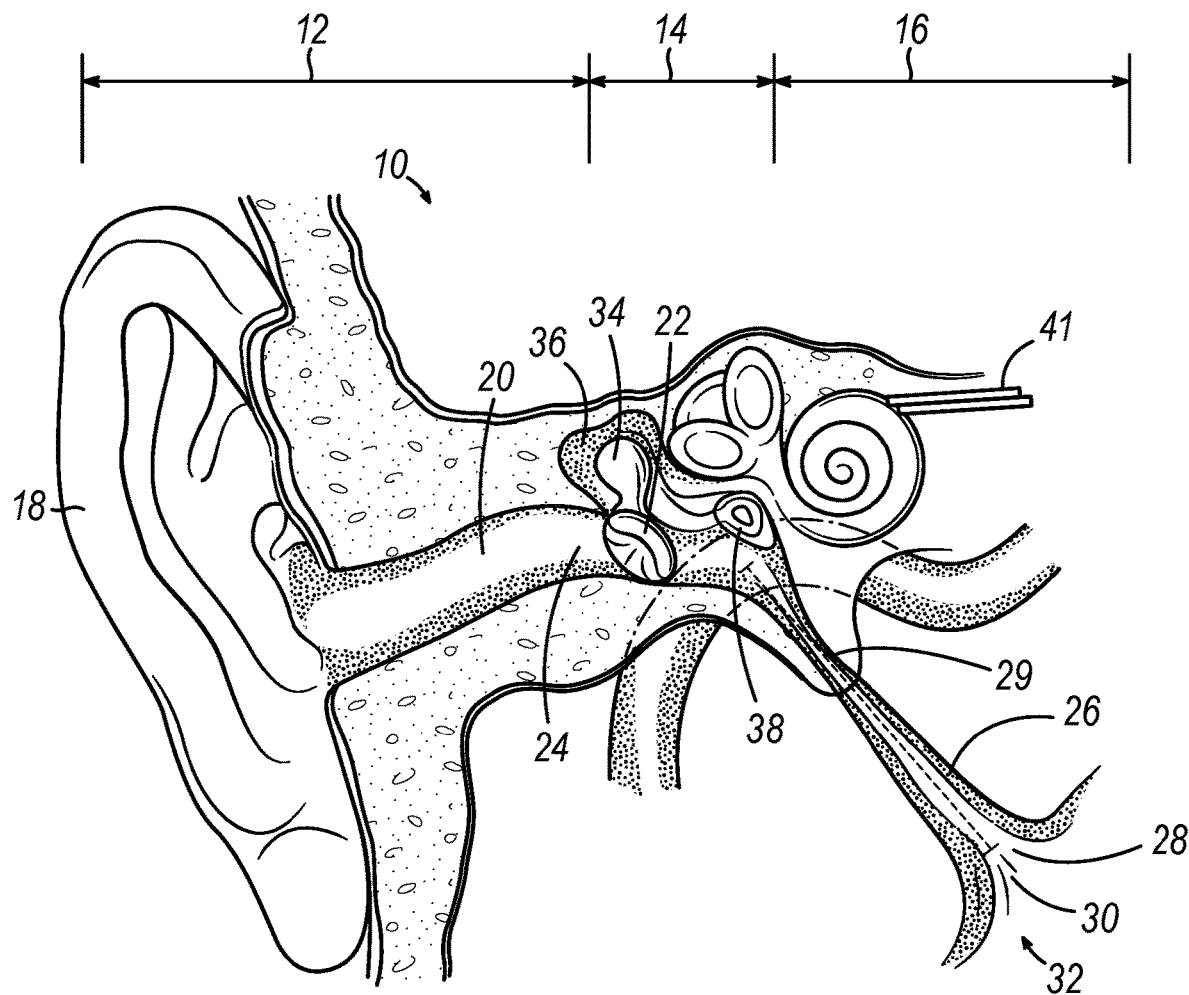
FIG. 1 depicts a cross-sectional view of a human ear showing an inner ear portion, a middle ear portion, an outer ear portion, and an ET in a patulous state connecting the middle ear portion with the nasopharynx region of the throat.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following detailed description should be read with reference to the drawings, in which like elements in different drawings are identically numbered. The drawings, which are not necessarily to scale, depict exemplary examples for the purpose of explanation only and are not intended to limit the scope of the invention. The detailed description illustrates by way of example, not by way of limitation, the principles of the invention. This description will clearly enable one skilled in the art to make and use the invention, and describes several examples, adaptations, variations, alternative and uses of the invention, including what is presently believed to be the best mode of carrying out the invention.

As used herein, the terms "about" and "approximately" for any numerical values or ranges indicate a suitable dimensional tolerance that allows the part or collection of components to function for its intended purpose as described herein.

It will be appreciated that the terms "proximal" and "distal" are used herein with reference to an operator gripping a deployment device.

I. Exemplary Method of Treating the Eustachian Tube

As noted above, PET is a physical disorder where the ET (26) remains patulous for a prolonged period, which may be undesirable for various reasons. In some instances, the method of treating PET uses a substance that dissolves into the tissue over time and may require another surgery. It may therefore be desirable to insert a more permanent device or implant into a pocket of tissue adjacent to the pharyngeal ostium (28). As described in the below examples, this device or implant may be a wire structure or a stent. Other suitable kinds of structures that may be used will be apparent to those skilled in the art in view of the teachings herein.

The following description provides various examples of the methods to deploying a device or implant into a pocket of tissue adjacent to the pharyngeal ostium (28) to constrict an inner diameter of the ET (26) from the isthmus (29) to the pharyngeal ostium (28). Other suitable ways in which the below-described methods may be carried out will be apparent to those skilled in the art in view of the teachings herein.

Figure 2:
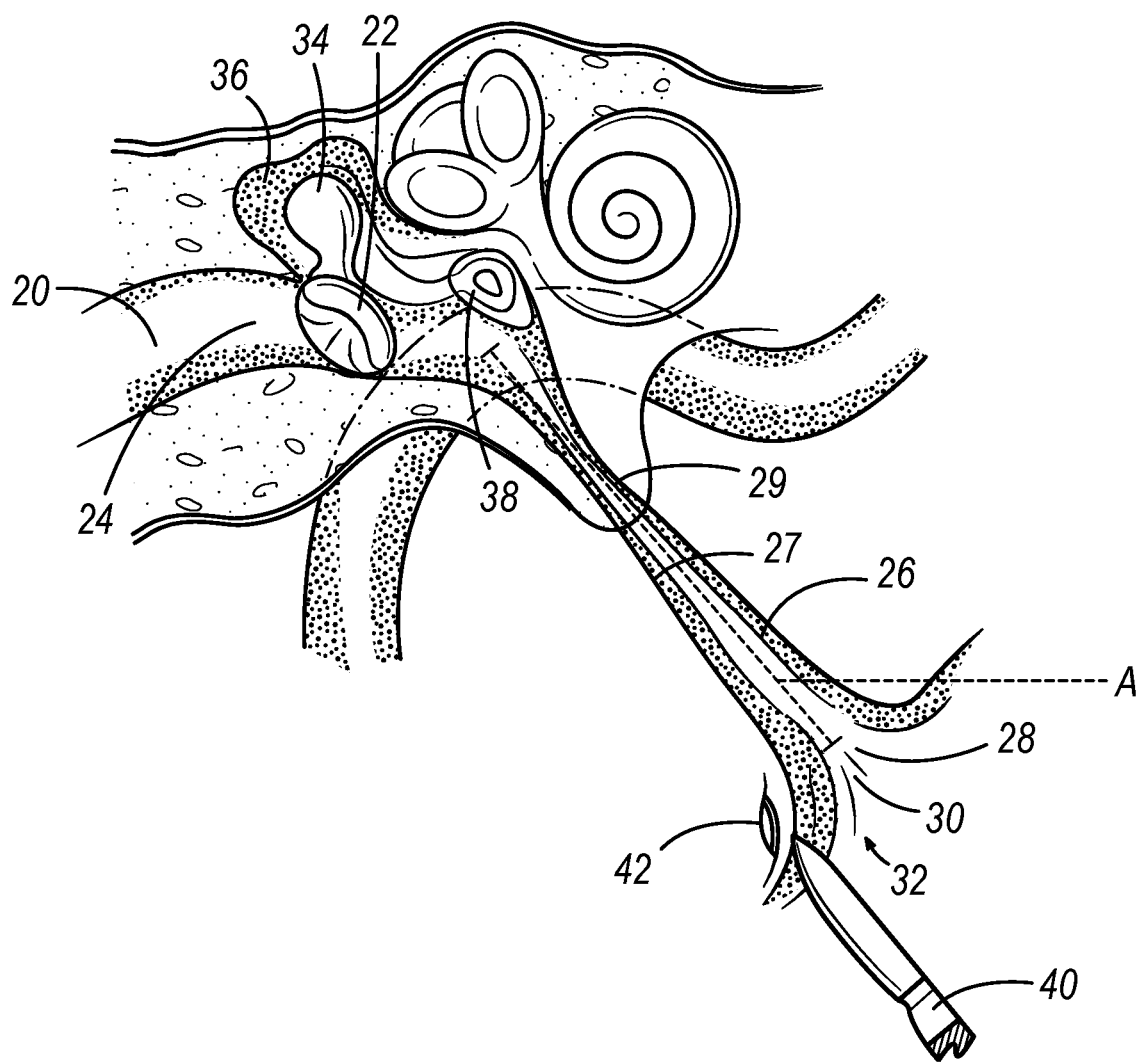
FIG. 2 depicts a cross-sectional view of a human ear showing the inner ear portion, the middle ear portion, and the ET with an incision being made into a region of tissue adjacent to the pharyngeal ostium.
Figure 3:
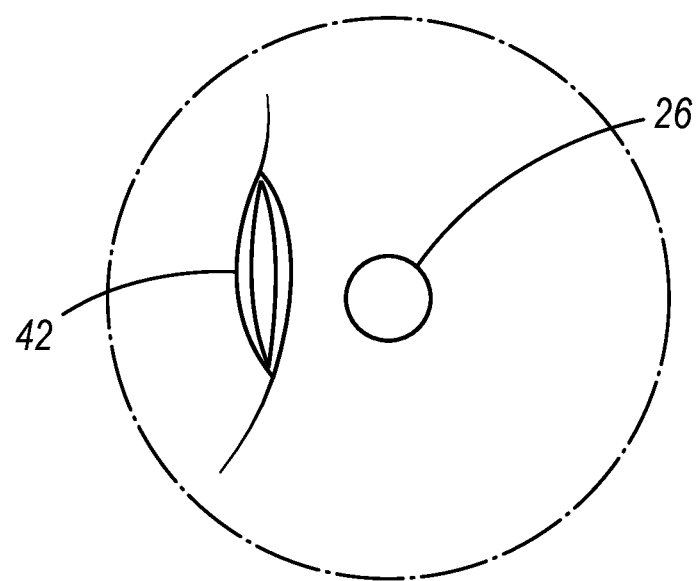
FIG. 3 depicts an enlarged end view of the incision and the pharyngeal ostium of FIG. 2.

A. Exemplary Method of Treating a Patulous Eustachian Tube with a Wire Structure FIG. 2 shows an operator making an incision (42) in the wall of the nasopharynx region (30) adjacent to the pharyngeal ostium (28) with a scalpel (40) (though any other suitable instrument may be used to form incision (42)). This procedure may be performed under visual guidance using an endoscope (not shown) or using any other suitable kind of visualization. In the present procedure, scalpel (40) may be advanced into a nostril and through a nasal cavity, or through the patient's throat, to position a distal end of scalpel (40) near the pharyngeal ostium (28). FIG. 3 shows an end view of the incision (42) formed by the scalpel (40), adjacent to the pharyngeal ostium (28).

Figure 4:
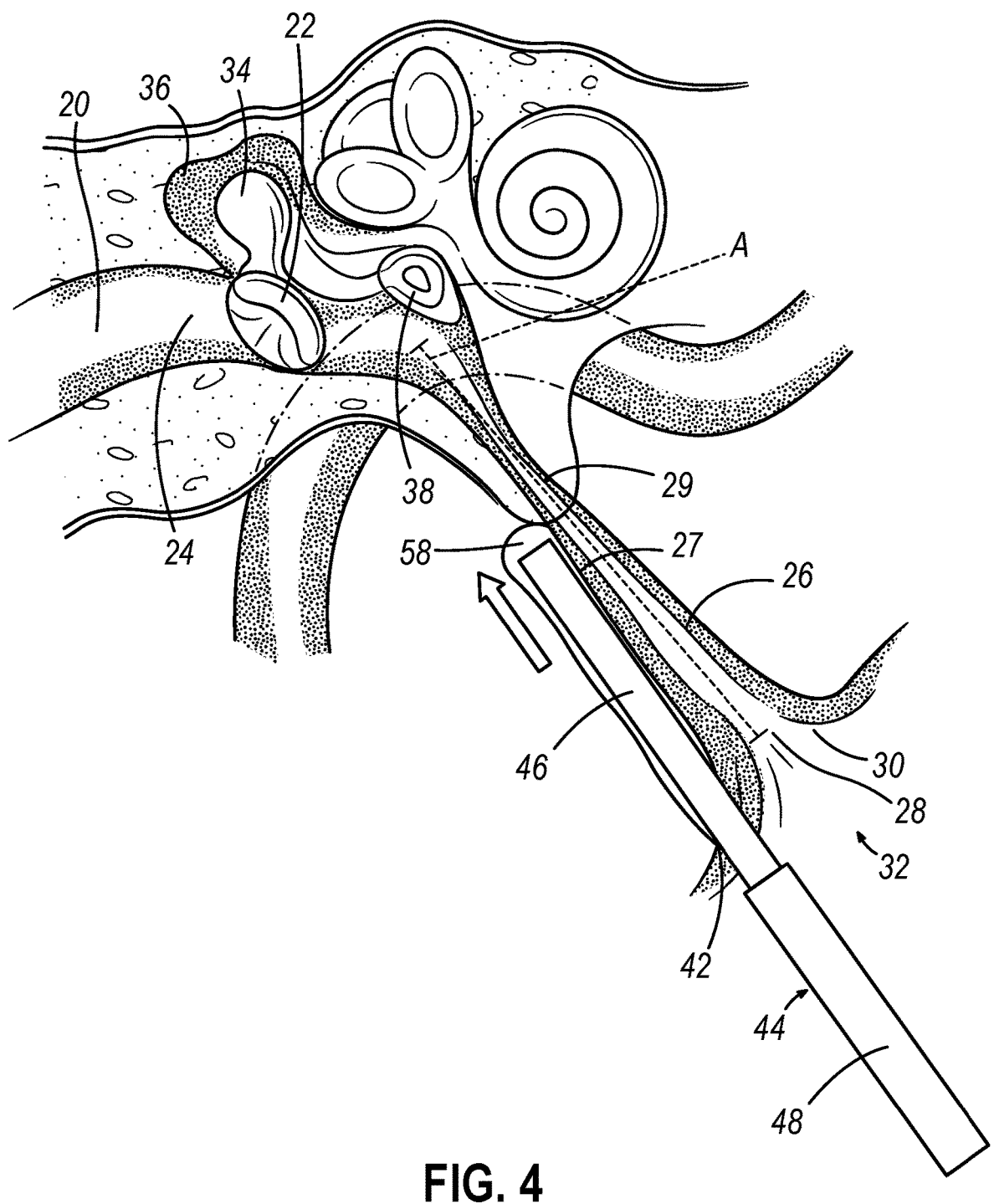
FIG. 4 depicts a cross-sectional view of a deployment device being inserted into the incision of FIG. 2 and creating a pocket.

FIG. 4 shows an operator using a deployment device (44), via the nostril or mouth, to enlarge a pocket (58) created parallel to a longitudinal axis (A) that extends through the ET (26) from the isthmus (29) to the pharyngeal ostium (28). This pocket (58) is separated from the ET (26) by a wall (27) of the ET (26). An operator can use a deployment device (44) that incorporates the ability to ream the pocket (58) and deploy an implant (52, 54), (see FIGS. 5 and 9 respectively); or the operator may use a designated surgical instrument (not shown) designed specifically for reaming or otherwise dissecting tissue. This designated surgical instrument (not shown) can be power actuated in some versions.

In some instances, deployment device (44) and wire structure (52) may be passed through a nostril to the ET (26) on the ipsilateral side (same side) of the head as the ET (26) that is being treated. An endoscope (not shown) may also be deployed through the ipsilateral side (same side) of the head. In some other instances, deployment device (44), and wire structure (52) may be passed through a nostril to the ET (26) on the contralateral side (opposite side) of the head as the ET (26) that is being treated. Similarly, an endoscope (not shown) may be passed through the contralateral (opposite side) of the head as the ET (26) that is being treated.

Figure 5:
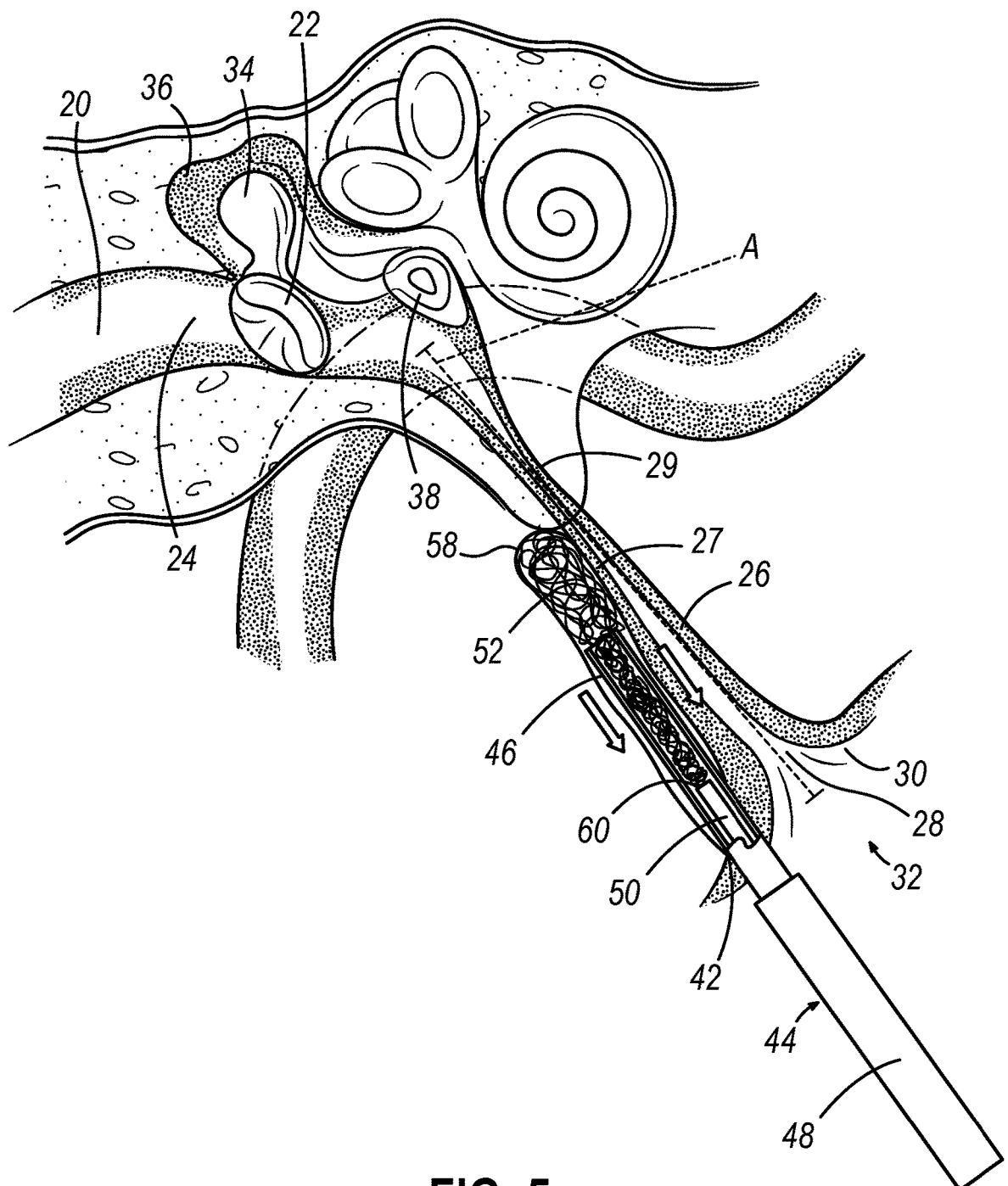
FIG. 5 depicts a cross-sectional view of a sheath of the deployment device of FIG. 4 being retracted and a wire structure deploying into the pocket created by the deployment device.

Deployment device (44) of the present example has a sheath (46), an outer cannula (48), and a rod (50) (see FIG. 5). Outer cannula (48) extends distally from the operator and can be malleably or rigidly bent to facilitate insertion into the nasopharynx region (30). Sheath (46) is configured to slidably extend distally from the outer cannula (48). Sheath (46) can have sharp edges on the open distal end of the sheath (46) that are configured to enlarge the pocket (58) when the deployment device (44) is in a first position, though this is merely optional. As another merely illustrative variation, the distal end of sheath (46) may be tapered to act like a mandrel by providing blunt dissection to enlarge the incision (42) and expand the pocket (58). In the first position, sheath (46) is locked in the linearly extended position. Pocket (58) is enlarged by linear movement (and, in some cases, rotational movement) of the deployment device (44) along a path that is parallel to longitudinal axis (A).

FIG. 5 shows the operator retracting sheath (46) into outer cannula (48) from an extended position to a retracted position. In some variations, sheath (46) may retract over outer cannula (48) instead of into outer cannula (48). Sheath (46) contains a rod (50) and a wire structure (52). Rod (50) extends longitudinally from the outer cannula (48) to a rod tip (60). Rod (50) is located at a proximal end of wire structure (52) and maintains the longitudinal position of wire structure (52) during the transition of the sheath (46) from the extended position to the retracted position. As sheath (46) transitions between the extended position and the retracted position, the wire structure (52) transitions from a compressed state to an expanded state. Wire structure (52) is resiliently biased to expand; and thereby fills pocket (58) as sheath (46) exposes the wire structure (52).

By way of example only, wire structure (52) may be configured like a conventional aneurysm coil, but with a size and configuration that is configured to fill the pocket (58) and urge the ET (26) to a closed state as described below. By way of further example only, wire structure (52) may be formed of nitinol or some other resilient material. Some versions of wire structure (52) are configured to remain in the patient indefinitely, such that wire structure (52) will not degrade or be bioabsorbed.

Figure 6:
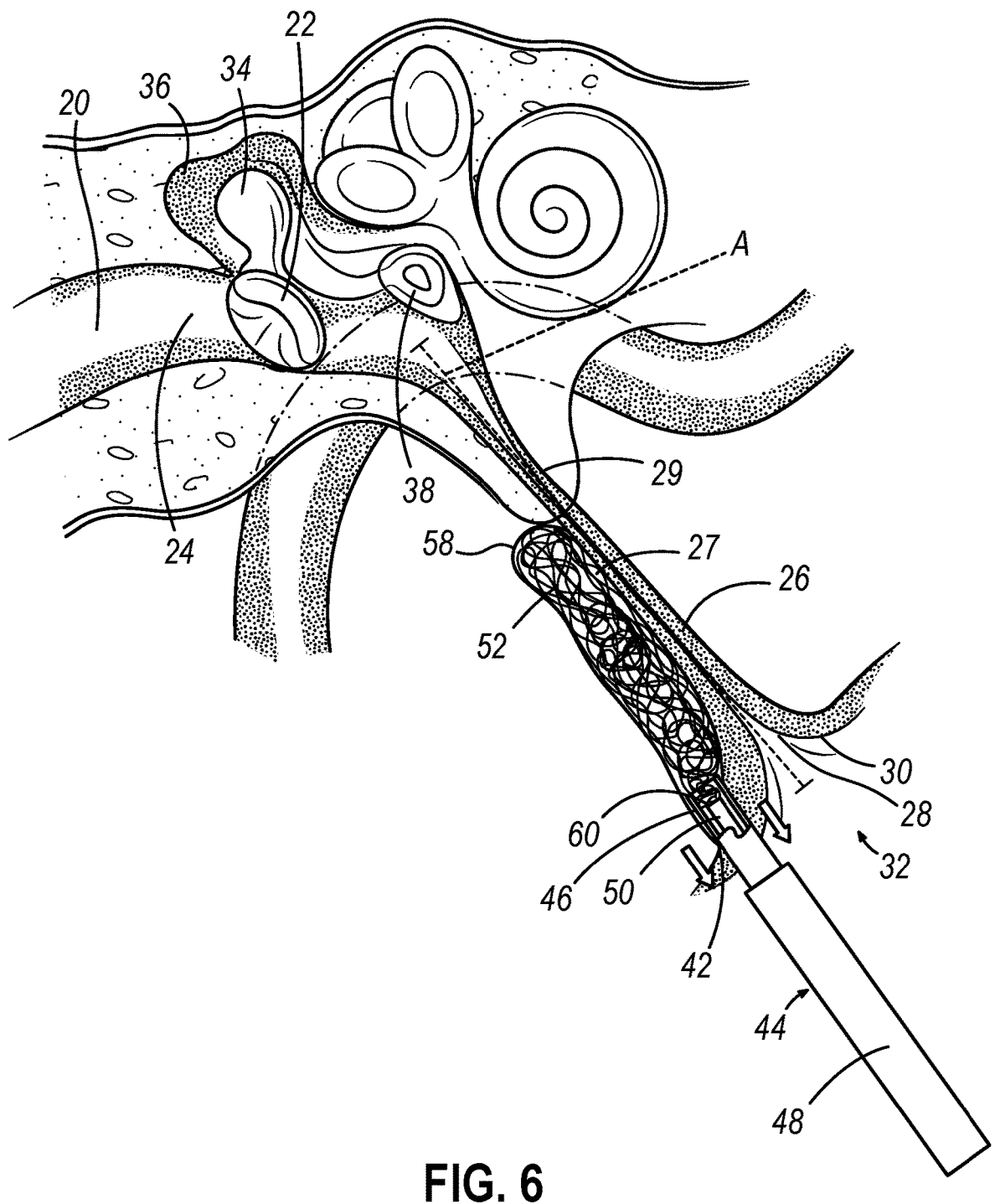
FIG. 6 depicts a cross-sectional view of the sheath of the deployment device of FIG. 4 fully retracted and the wire structure of FIG. 5 expanding into the pocket created in FIG. 4.
Figure 7:
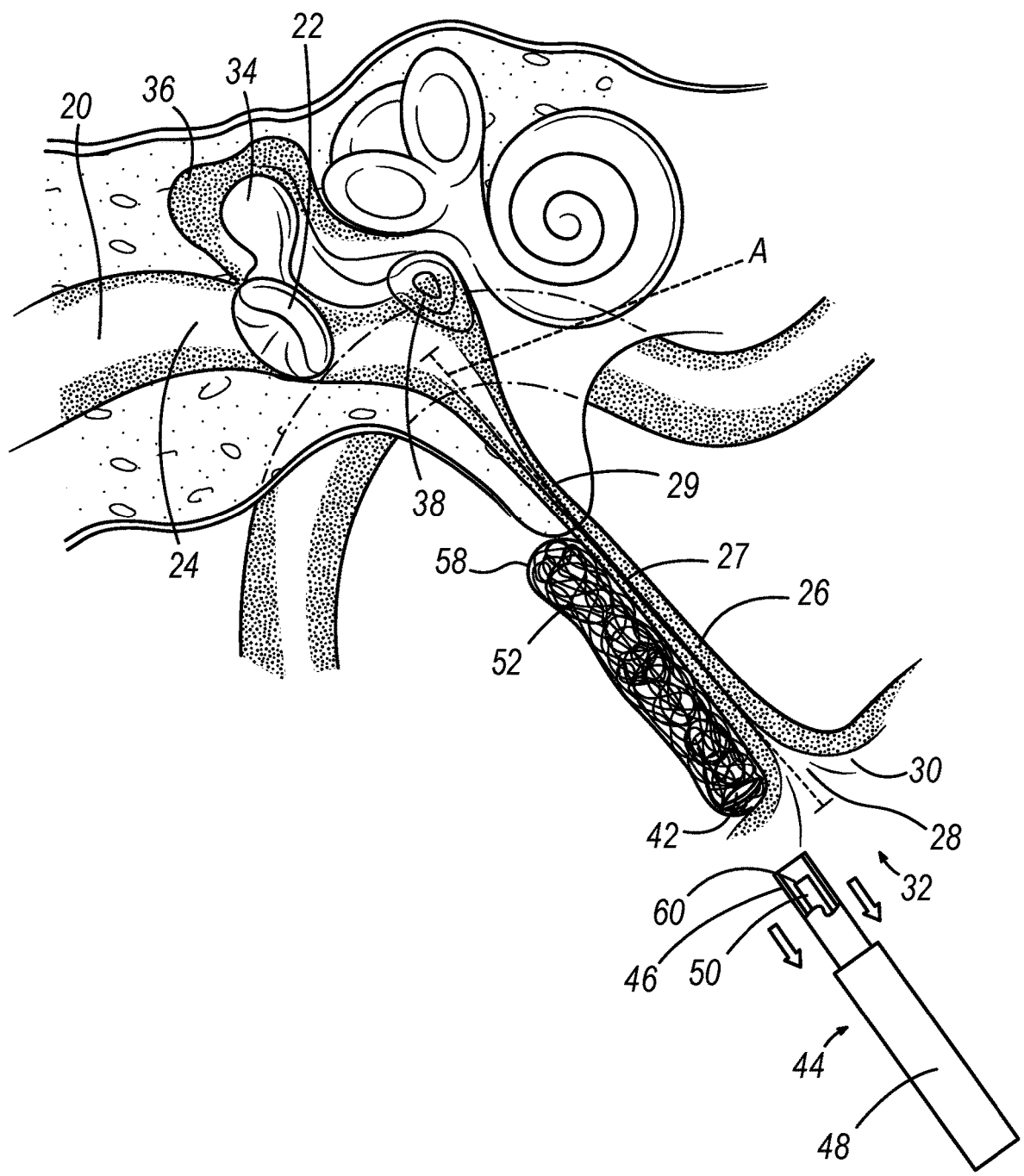
FIG. 7 depicts a cross-sectional view of the deployment device being removed from the pocket created in FIG. 4.

FIG. 6 and FIG. 7 shows the sheath (46) in the retracted position. Wire structure (52) continues to expand and biases pocket (58) radially outwardly. FIG. 7 shows the operator removing deployment device (44) from the pocket (58).

Figure 8:
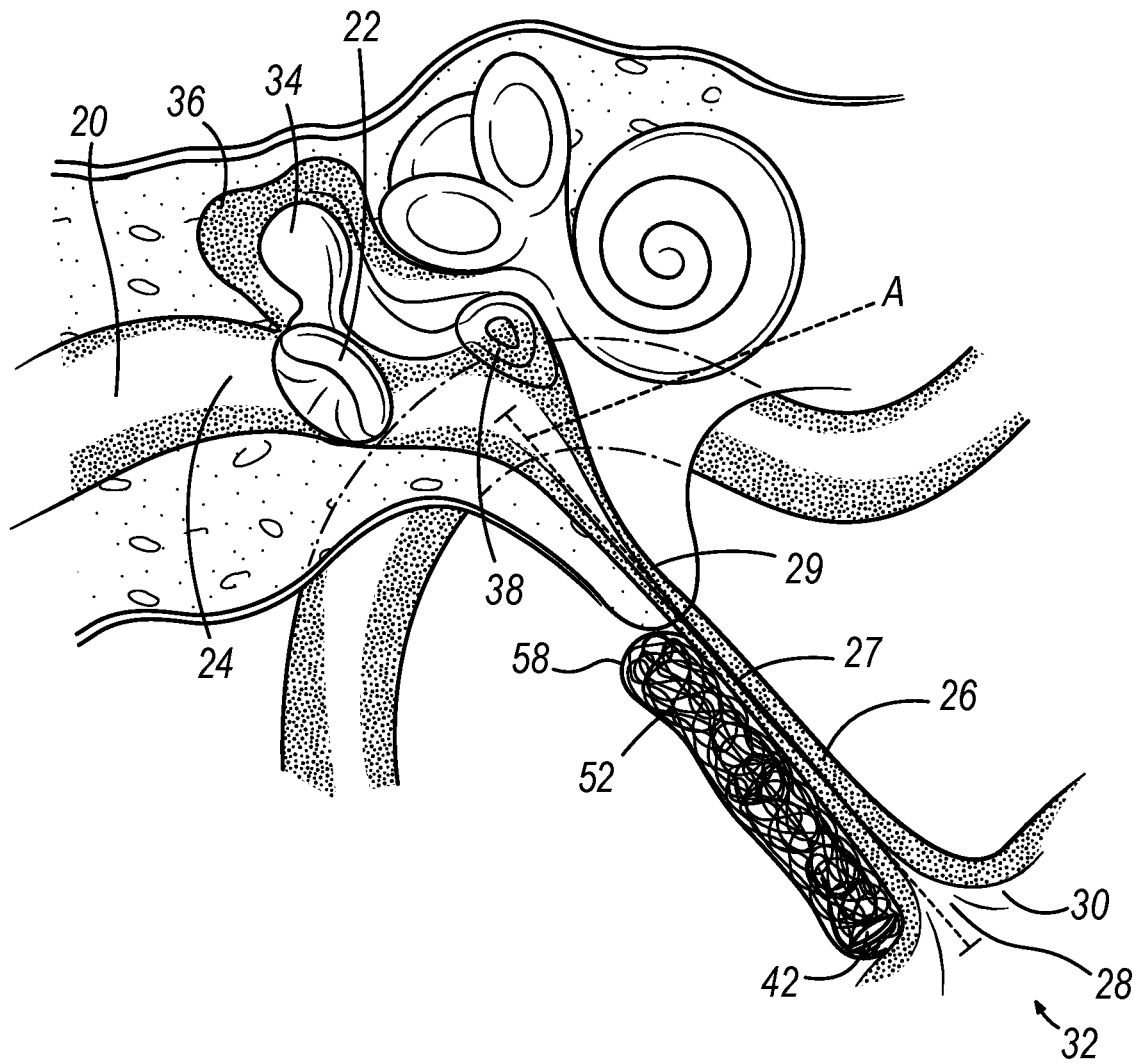
FIG. 8 depicts a cross-sectional view of the wire structure of FIG. 5 urging the ET into a closed state.

FIG. 8 shows the wire structure (52) deployed parallel to the longitudinal axis (A) that extends through the ET (26) from the isthmus (29) to the pharyngeal ostium (28); proximate to wall (27) of ET (26). Wire structure (52) biases the pocket (58) radially outwardly. Because the pocket (58) is proximate and parallel to the wall (27) of the ET (26) and only separated from the ET (26) by the wall (27), the expanded wire structure (52) urges the ET (26) to a closed state. The opening of the pocket (58) may be sutured, glued shut, or cauterized to close the opening (42) of pocket (58) to ensure retention of wire structure (52) in the pocket (58).

With the implanted wire structure (52) bearing against the wall (27) of the ET (26) and thereby resiliently urging the ET (26) to a closed state, the implanted wire structure (52) may effectively treat an otherwise patulous ET (26). Moreover, the resilience of the implanted wire structure (52) may allow the ET (26) to still selectively slightly open under normal conditions (e.g., when the patient swallows or yawns, etc.). Thus, in some instances, the implantation of wire structure (52) does not necessarily result in the ET (26) being in a permanently closed state. While the above description includes an example of wire structure (52) being nondegradable (e.g., such that wire structure (52) permanently or indefinitely remains in the patient), some versions of wire structure (52) may be degradable. In such versions, wire structure (52) may nevertheless be configured to promote the creation of scar tissue in and/or around the pocket (58). In such instances, the scar tissue may assist in substantially maintaining the ET (26) in a closed state (while still allowing the ET (26) to still selectively slightly open under normal conditions).

Figure 9:
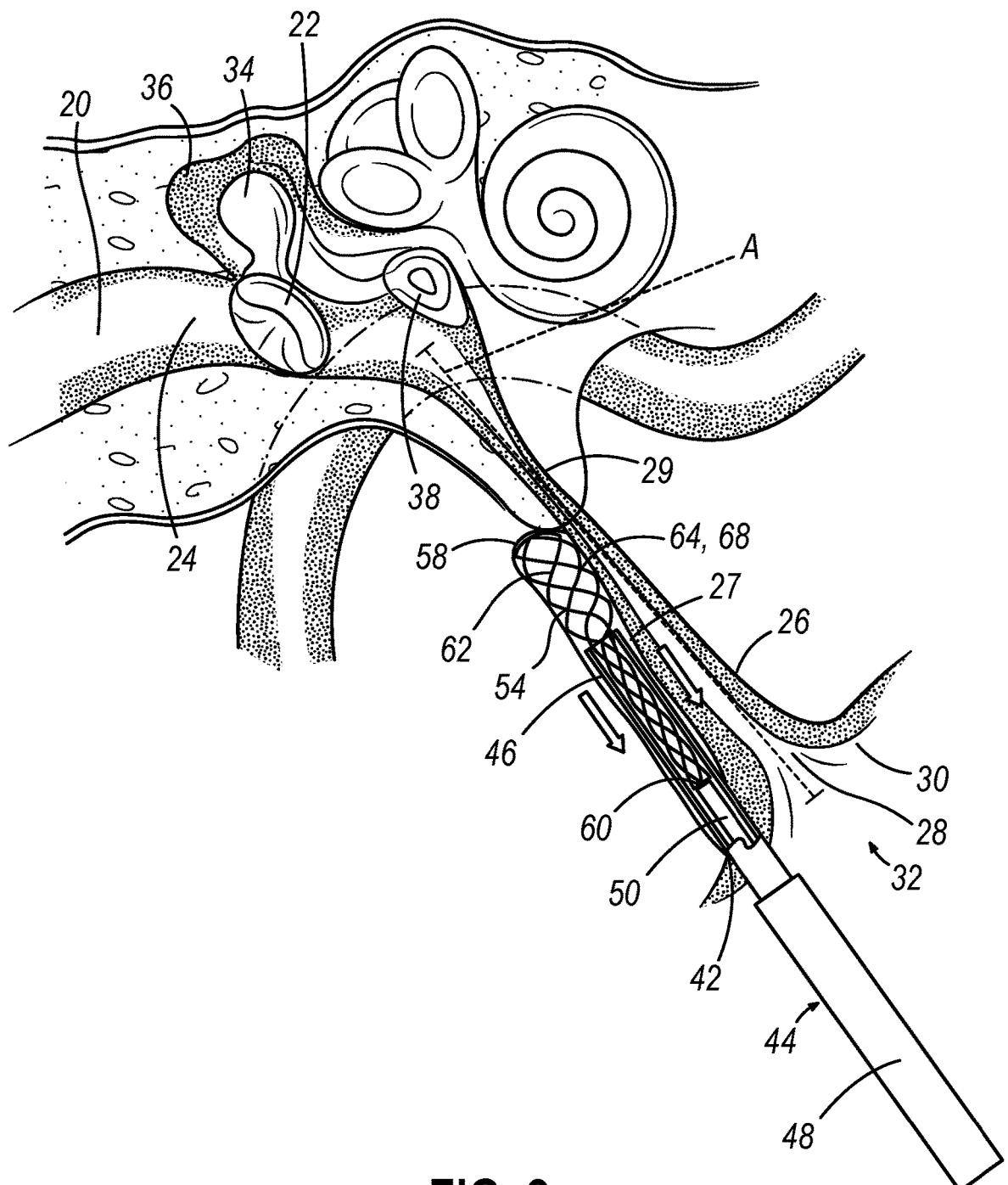
FIG. 9 depicts a cross-sectional view of the sheath of the deployment device of FIG. 4 retracting and a stent deploying into a pocket created by the deployment device.

B. Exemplary Method of Treating a Patulous Eustachian Tube with a Self-Expanding Stent FIG. 9 shows another instance of an operator retracting sheath (46) into an outer cannula (48) from an extended position to a retracted position, where sheath (46) is disposed in a pocket (58) adjacent to the pharyngeal ostium (28) and the ET (26). As described above, sheath (46) contains a rod (50) and a stent (54). Rod (50) extends longitudinally from the outer cannula (48) to a rod tip (60). Rod (50) is located at a proximal end of wire structure (52) and maintains the longitudinal position of the stent (54) during movement of sheath (46) from the extended position to the retracted position. As sheath (46) transitions from the extended position to the retracted position, the stent (54) transitions accordingly from a compressed state to an expanded state. Stent (54) is resiliently biased toward the expanded state and thereby expands outwardly against the sidewall of the pocket (58) as sheath (46) exposes the stent (54).

Figure 10:
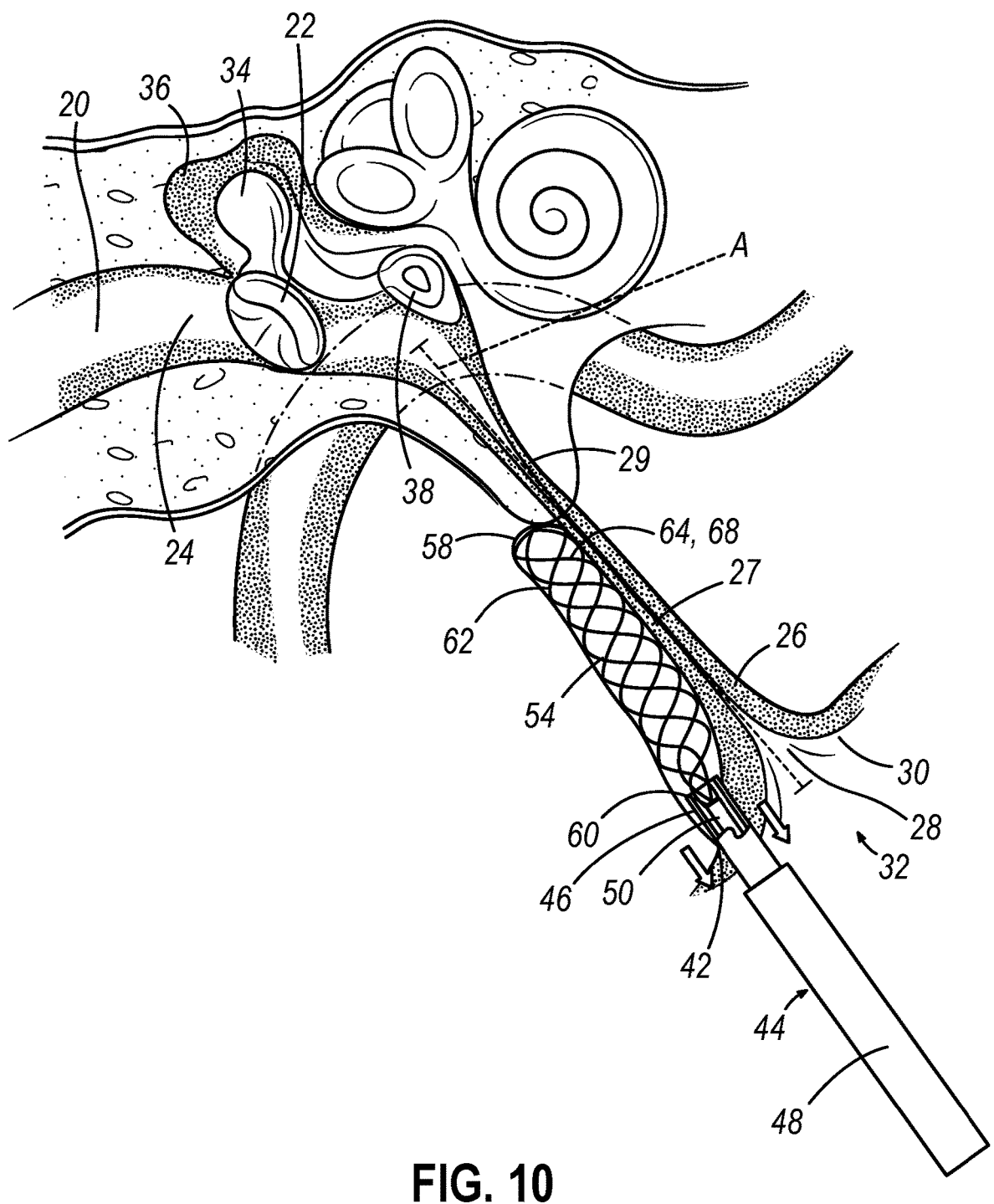
FIG. 10 depicts a cross-sectional view of the sheath of the deployment device of FIG. 4 fully retracted and the stent of FIG. 9 expanding in the pocket.

FIG. 10 shows sheath (46) of deployment device (44) in the retracted position. Stent (54) is an elongate, cylindraceous device that is configured to resiliently expand outwardly like various conventional stents. Stent (54) includes a plurality of longitudinal struts (62) in a woven or looped arrangement such that each longitudinal strut (62) of the plurality of struts (62) is immediately adjacent to another longitudinal strut (62) thereby forming a mesh design or pattern. The mesh pattern of surfaces (64) is configured to accommodate and allow for the expandability of stent (54). In other words, stent (54) is configured to be radially expandable from the selective separation and extension of the plurality of longitudinal struts (62) along surfaces (64).

Stent (54) is configured to have a flexible configuration such that stent (54) is both expandable and easily maneuverable while in a contracted state for implantation within a patient's body, for example, in a pocket (58) formed adjacent and parallel to an ET (26). Surfaces (64) of stent (54) may be formed of a metal bio-absorbable material. Moreover, surfaces (64) may be coated with a biocompatible polymer coating. As merely an illustrative example, stent (54) may be formed of Resoloy®, a bioresorbable magnesium-alloy manufactured by MeKo Laster Material Processing, Hannover, Germany. As another merely illustrative alternative, stent (54) may be formed of nitinol. Alternatively, for example, stent (54) may be formed of a biodegradable thermoplastic such as polylactic acid. In either instance, by being formed of a biocompatible material, stent (54) can be configured to degrade within a patient's body after a predetermined degradation time. In other examples, stent (54) may be formed of a non-degradable material such that stent (54) is required to be manually removed; or such that stent (54) remains in the patient's body permanently or otherwise indefinitely.

Stent (54) is further formed of a material that includes shape memory and/or elastic characteristics suitable for insertion into a patient's body. With the shape memory characteristics, stent (54) is resiliently biased to deform outwardly back to the default, expanded state after the selective expansion of surfaces (64) to the expanded state. In this instance, stent (54) has a resilient strength that is naturally inclined to transform back to an original contracted state up to a predetermined strength, such that stent (54) returns to the expanded state despite the presence of an intervening restraint or counter force applied thereon. As merely an illustrative example, stent (54) may be formed of an alloy such as Nitinol that includes shape memory and/or superelastic characteristics.

Stent (54) is further shaped and sized to allow stent (54) to slidably advance into the pocket (58) when in the contracted state. Stent (54) can further include a tissue binding coating (68) along exterior surface (64). Tissue binding coating (68) is operable to fasten stent (54) against adjacent tissue upon the tissue contacting surface (64). As such, stent

(54) is configured to securely engage an adjacent tissue upon selectively abutting surface (64) along the adjacent tissue. By way of example only, tissue binding coating (68) may comprise isocyanate, cyanoacrylate, and/or any other suitable biocompatible adhesive. Other suitable materials that may be used will be apparent to those skilled in the art in view of the teachings herein. Although not shown, it should be understood that other fastening means or mechanisms may be included along surface (64) to thereby allow stent (54) to securely attach to an adjacent tissue. For example, stent (54) may include barbs or other mechanical anchoring features along exterior surface (64) that are configured to fasten stent (54) to pocket (58).

Figure 11:
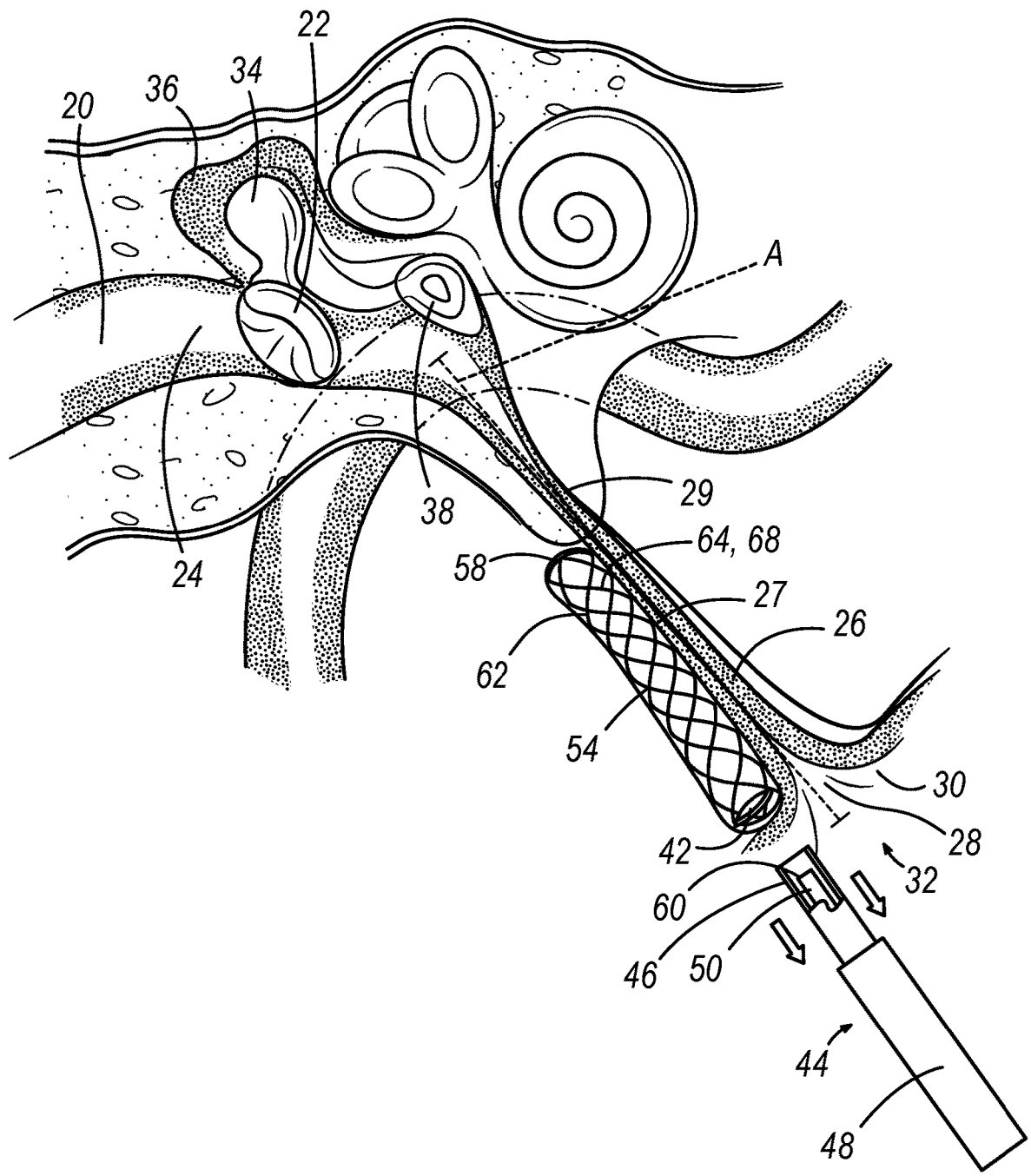
FIG. 11 depicts a cross-sectional view of the deployment device being removed from the pocket created in FIG. 9.
Figure 12:
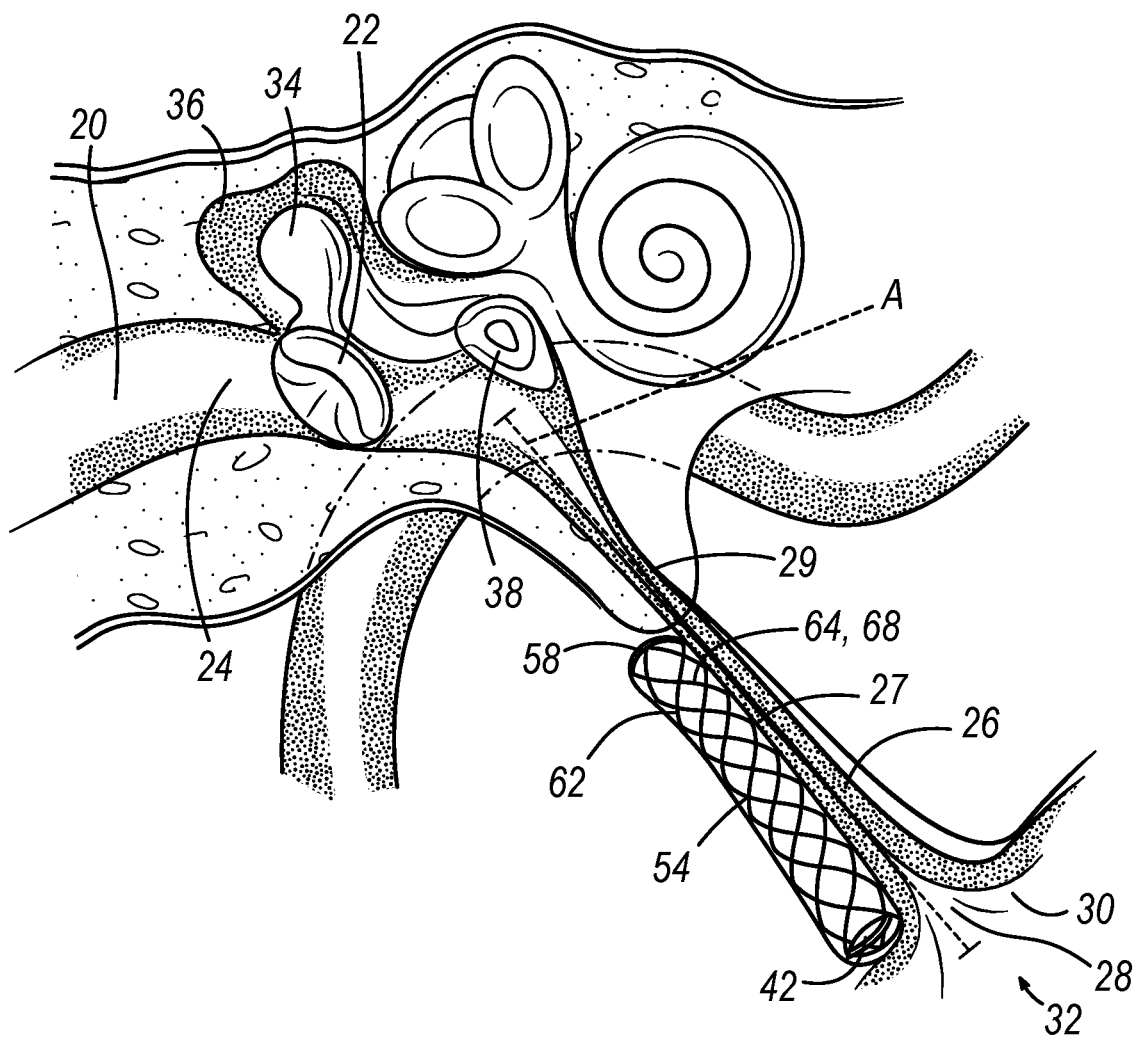
FIG. 12 depicts a cross-sectional view of the stent of FIG. 9 fully expanded in the pocket and urging the ET into a closed state.

In the present example, as seen in FIG. 11, once stent (54) is deployed by deployment device (44), deployment device (44) is removed from pocket (58). FIG. 12 shows stent (58) deployed parallel to longitudinal axis (A). The stent (58) in the expanded state biases pocket (58) radially outwardly. Because the pocket (58) is proximate and parallel to the wall (27) of the ET (26) and only separated from the ET (26) by the wall (27), expanded stent (54) urges ET (26) to a closed state. The opening of the pocket (58) may be sutured, glued shut, or cauterized to close the opening (42) of pocket (58) to ensure retention of stent (54) in the pocket (58).

With the implanted stent (54) bearing against the wall (27) of the ET (26) and thereby resiliently urging the ET (26) to a closed state, the implanted wire structure (52) may effectively treat an otherwise patulous ET (26). Moreover, the resilience of the implanted stent (54) may allow the ET (26) to still selectively slightly open under normal conditions (e.g., when the patient swallows or yawns, etc.). Thus, in some instances, the implantation of stent (54) does not necessarily result in the ET (26) being in a permanently closed state. In versions where stent (54) is biodegradable, stent (54) may be configured to promote the creation of scar tissue in and/or around the pocket (58). In such instances, the scar tissue may assist in substantially maintaining the ET (26) in a closed state (while still allowing the ET (26) to still selectively slightly open under normal conditions).

Figure 13:
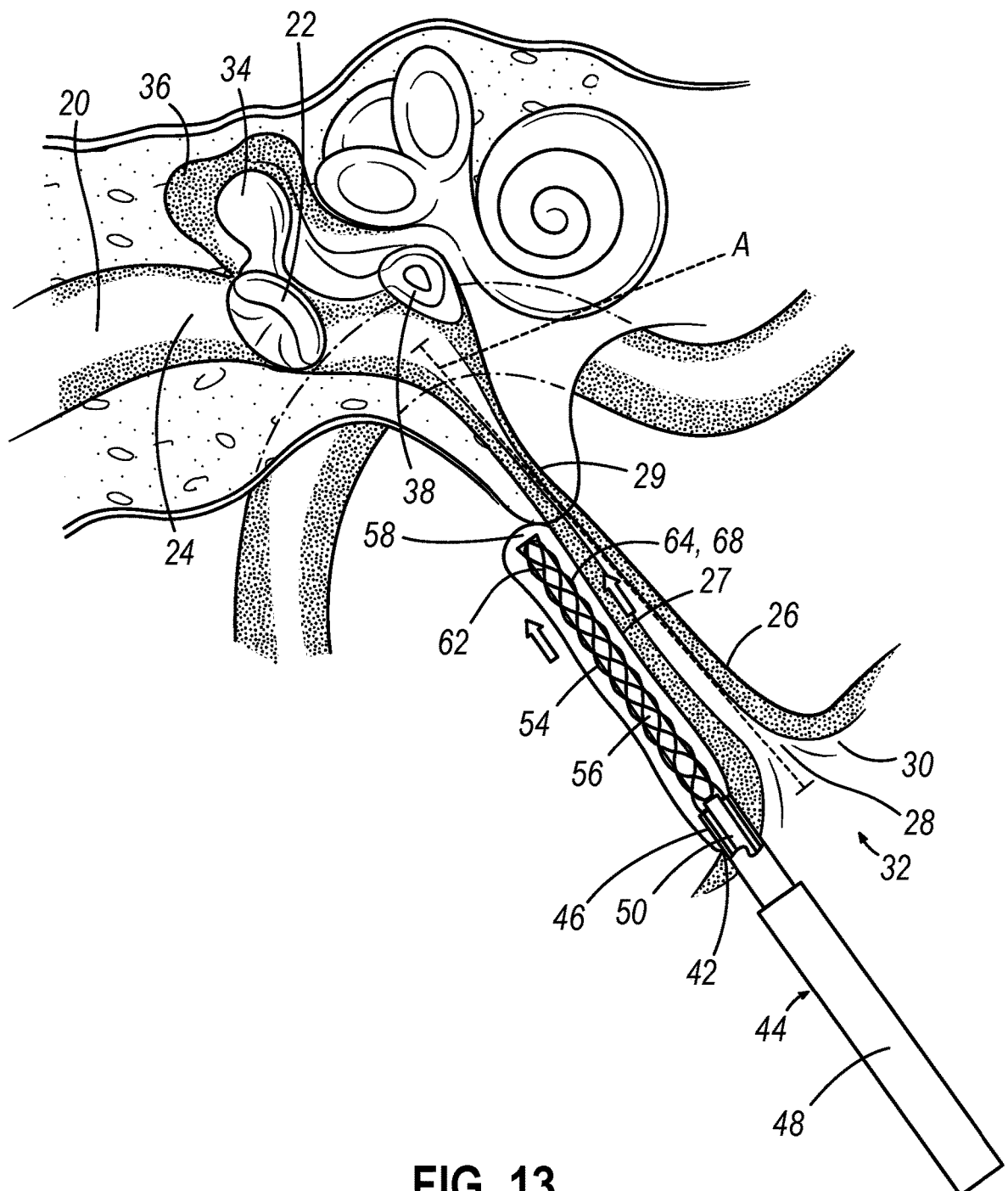
FIG. 13 depicts a cross-sectional view of a deployment device having a balloon dilation catheter with the balloon in a deflated state to slidably position a stent in a pocket formed adjacent to the pharyngeal ostium.

C. Exemplary Method of Treating a Patulous Eustachian Tube with Stent Deployed by a Balloon Catheter FIG. 13 shows another variation where deployment device (44) and stent (54) are cooperatively used to treat a patuolous ET (26) under visual guidance of an endoscope (not shown). The operator advances deployment device (44) into the nostril through the nasal cavity or into the mouth through the throat to position a distal end of deployment device (44) into incision (42) (see FIG. 2). The operator has enlarged pocket (58) with deployment device (44) or some other device (see FIG. 4) and has transitioned sheath (46) from an extended position (see FIG. 4) to a retracted position (see FIG. 6).

Prior to insertion, the operator positioned stent (54) on a balloon (56) of deployment device (44) such that stent (54) advances unitarily with deployment device (44) into the ET (26) while being carried on the balloon (56). Balloon (56) is located distal to outer cannula (48) and is disposed around rod (50). Stent (54) is disposed around balloon (56). An adhesive and/or other feature(s) may be used to removably secure stent (54) to balloon (56). Deployment device (44) is positioned such that balloon (56) and stent (54) are located in pocket (58), with balloon (56) in a non-expanded or partially expanded state, and with stent (54) in a contracted state.

In some instances, deployment device (44), balloon (56), and stent (54) may be passed through a nostril to the ET (26) on the ipsilateral side (same side) of the head as the ET (26) that is being treated. An endoscope (not shown) may also be deployed through the ipsilateral side (same side) of the head. In some other instances, deployment device (44), balloon (56) and stent (54) may be passed through a nostril to the ET (26) on the contralateral side (opposite side) of the head as the ET (26) that is being treated. Similarly, an endoscope (not shown) may be passed through the contralateral (opposite side) of the head as the ET (26) that is being treated.

Figure 14:
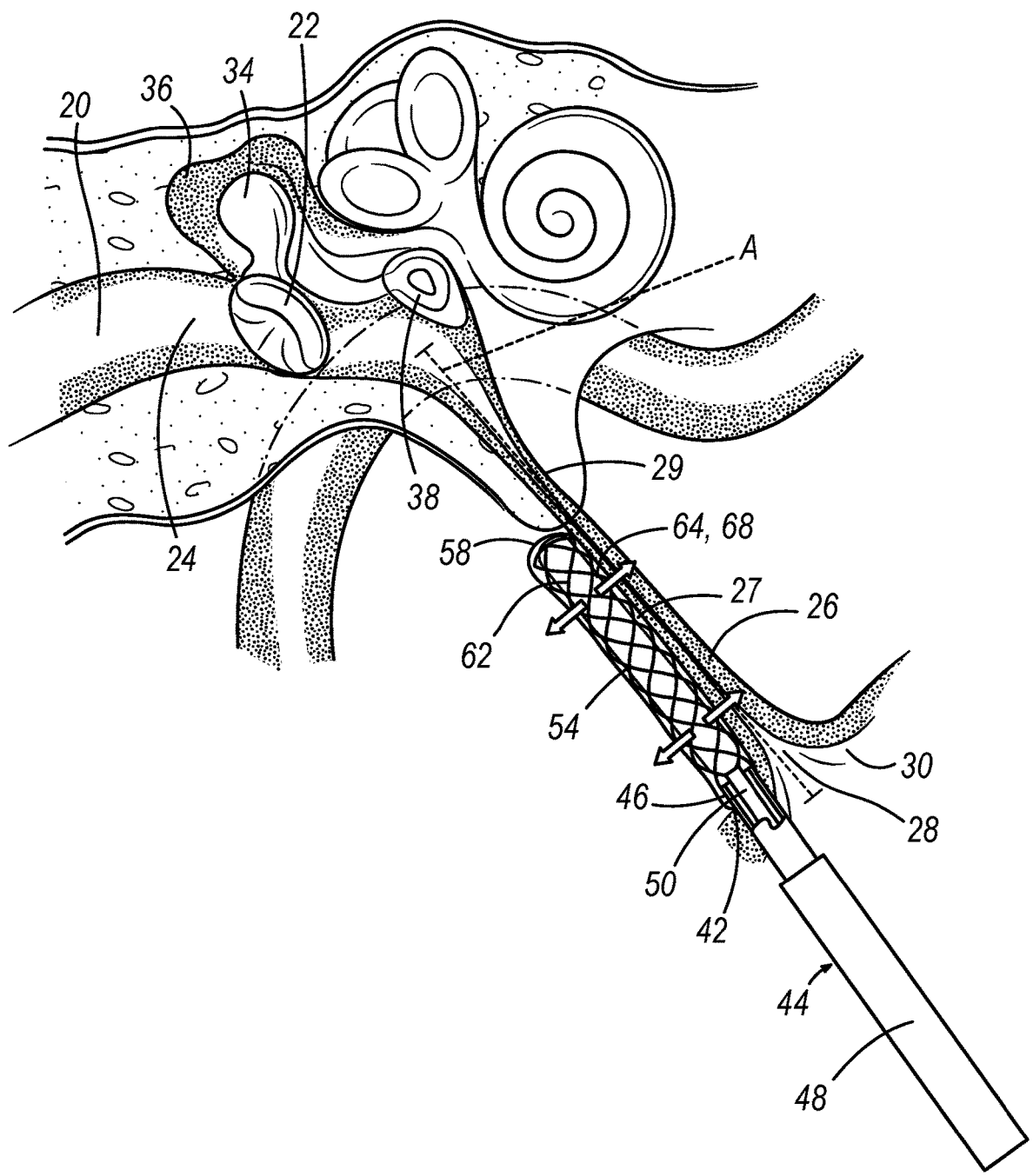
FIG. 14 depicts a cross-sectional view of the deployment device of FIG. 13 with the balloon in an inflated state to expand the stent in the pocket.

FIG. 14 shows balloon (56) transitioning from a contracted state to an expanded state. After balloon (56) is positioned within the pocket (58) and balloon (56) is inflated to an expanded state, balloon (56) may be held in a location while in an expanded state for an extended period (e.g. several seconds or minutes). The deployment device (44) may also deliver a substance to the pocket (58), such as one or more therapeutic agents. Balloon (56) of deployment device (44) is in fluid communication with an inflation lumen (not shown) located within outer cannula (48). The inflation lumen (not shown) is used for inflation of the balloon (56) with water, contrast medium, or saline.

Figure 15:
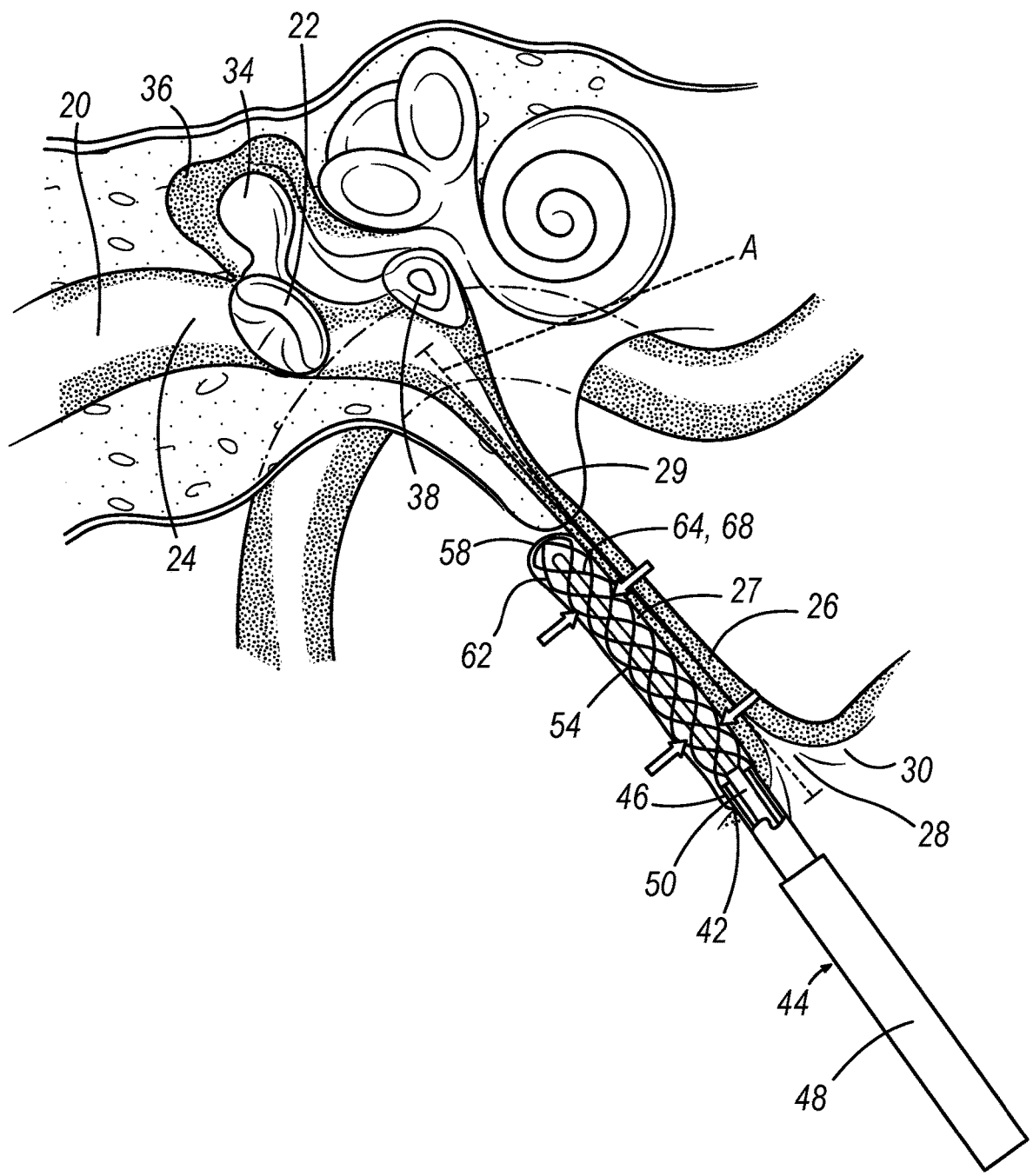
FIG. 15 depicts a cross-sectional view of the deployment device of FIG. 13 with the balloon in the deflated state and the stent remaining in expanded state in the pocket.

FIG. 15 shows balloon (56) transitioning from the expanded state to the contracted state. The stent (54) remains in the expanded state biasing pocket (58) radially outwardly. This variation of stent (54) shown in FIGS. 13-16 differs from the previously described variation of stent (54) shown in FIG. 9-12. Stent (54) shown in FIGS. 9-12 is resiliently biased to expand outwardly. By contrast, in this variation of stent (54) shown in FIG. 13-16, stent (54) is malleable, such that the expansion of balloon (56) drives expansion of stent (54); and stent (54) malleably retains the expanded state after stent (54) is expanded by balloon (56).

Figure 16:
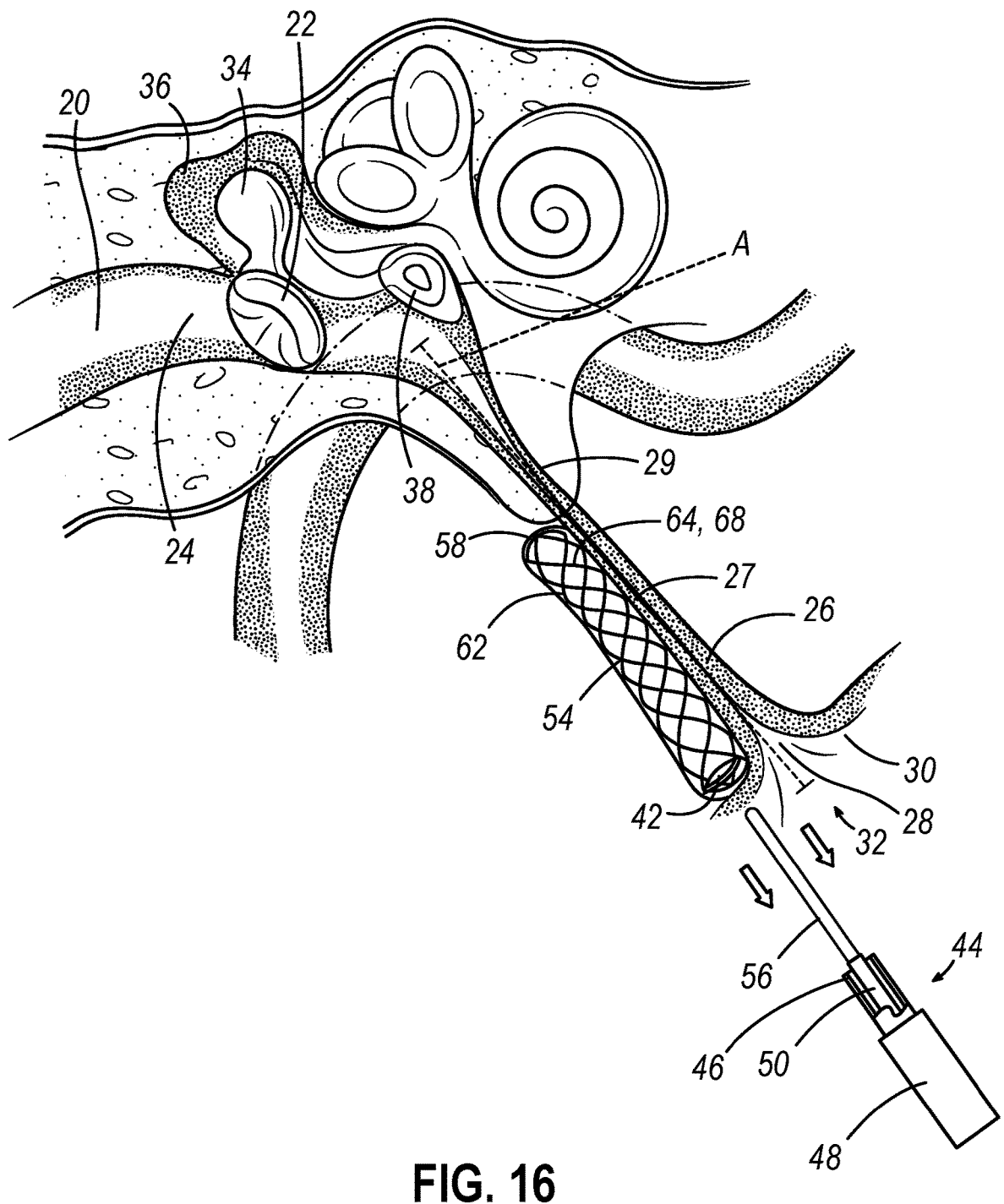
FIG. 16 depicts a cross-sectional view of the deployment device of FIG. 13 being removed from the pocket.

FIG. 16 shows deployment device (44) being removed from pocket (58). Because pocket (58) is proximate and parallel to the wall (27) of the ET (26) and only separated from the ET (26) by the wall (27), the expanded stent (54) urges the ET (26) to a closed state. The opening of the pocket (58) may be sutured, glued shut, or cauterized to close the opening (42) of pocket (58) to ensure retention of stent (54) in the pocket (58).

With the implanted stent (54) bearing against the wall (27) of the ET (26) and thereby urging the ET (26) to a closed state, the implanted stent (54) may effectively treat an otherwise patulous ET (26). Moreover, despite the malleability of stent (54), stent (54) may still have sufficient flexibility to allow the ET (26) to still selectively slightly open under normal conditions (e.g., when the patient swallows or yawns, etc.). Thus, in some instances, the implantation of stent (54) does not necessarily result in the ET (26) being in a permanently closed state. While the above description includes an example of stent (54) being nondegradable (e.g., such that stent (54) permanently or indefinitely remains in the patient), some versions of stent (54) may be degradable. In such versions, stent (54) may nevertheless be configured to promote the creation of scar tissue in and/or around the pocket (58). In such instances, the scar tissue may assist in substantially maintaining the ET (26) in a closed state (while still allowing the ET (26) to still selectively slightly open under normal conditions).

Figure 17:
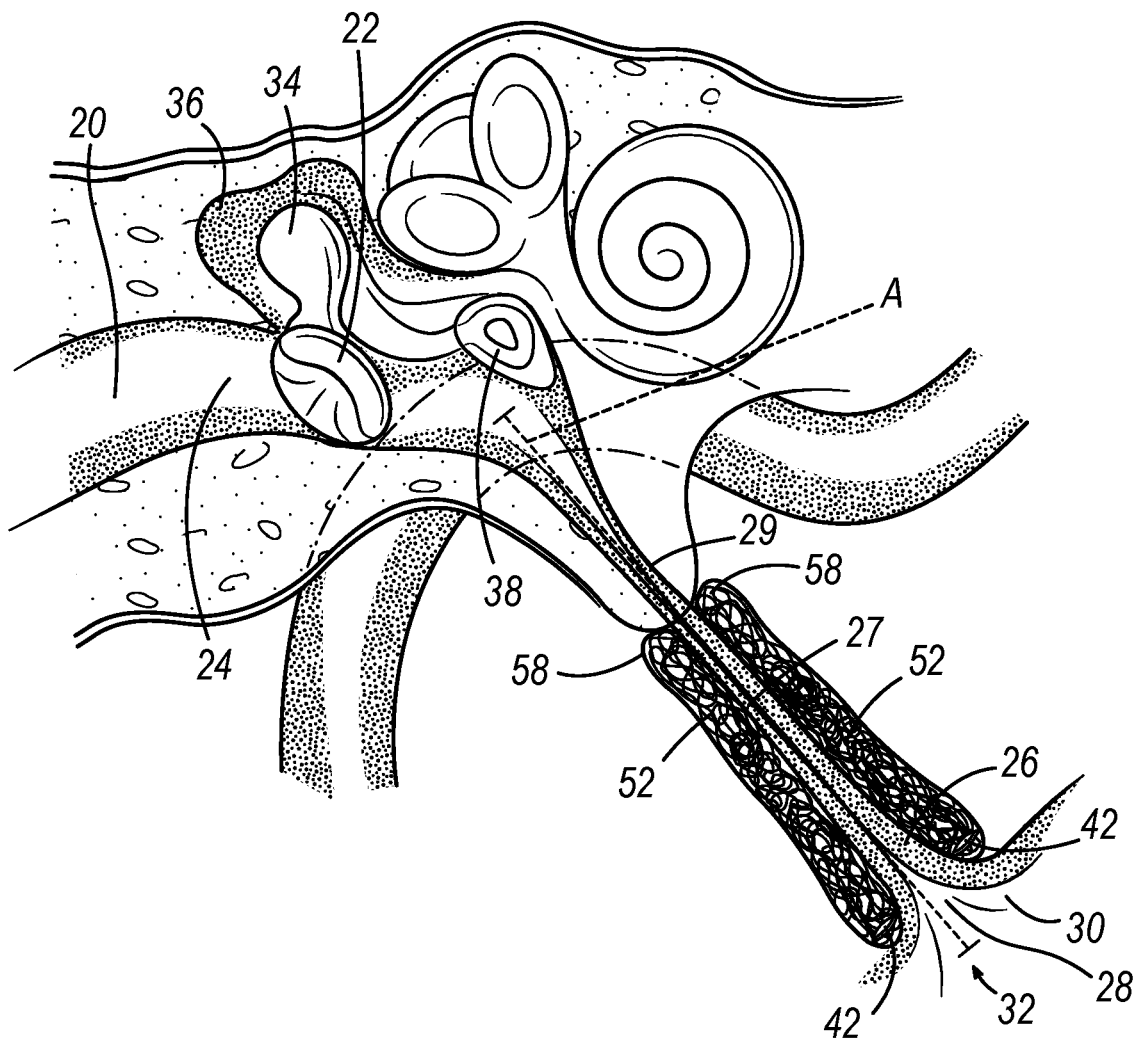
FIG. 17 depicts a cross-sectional view of an ET with two adjacent pockets containing wire structures in an expanded state to opposingly urge the ET to a closed state.
Figure 18:
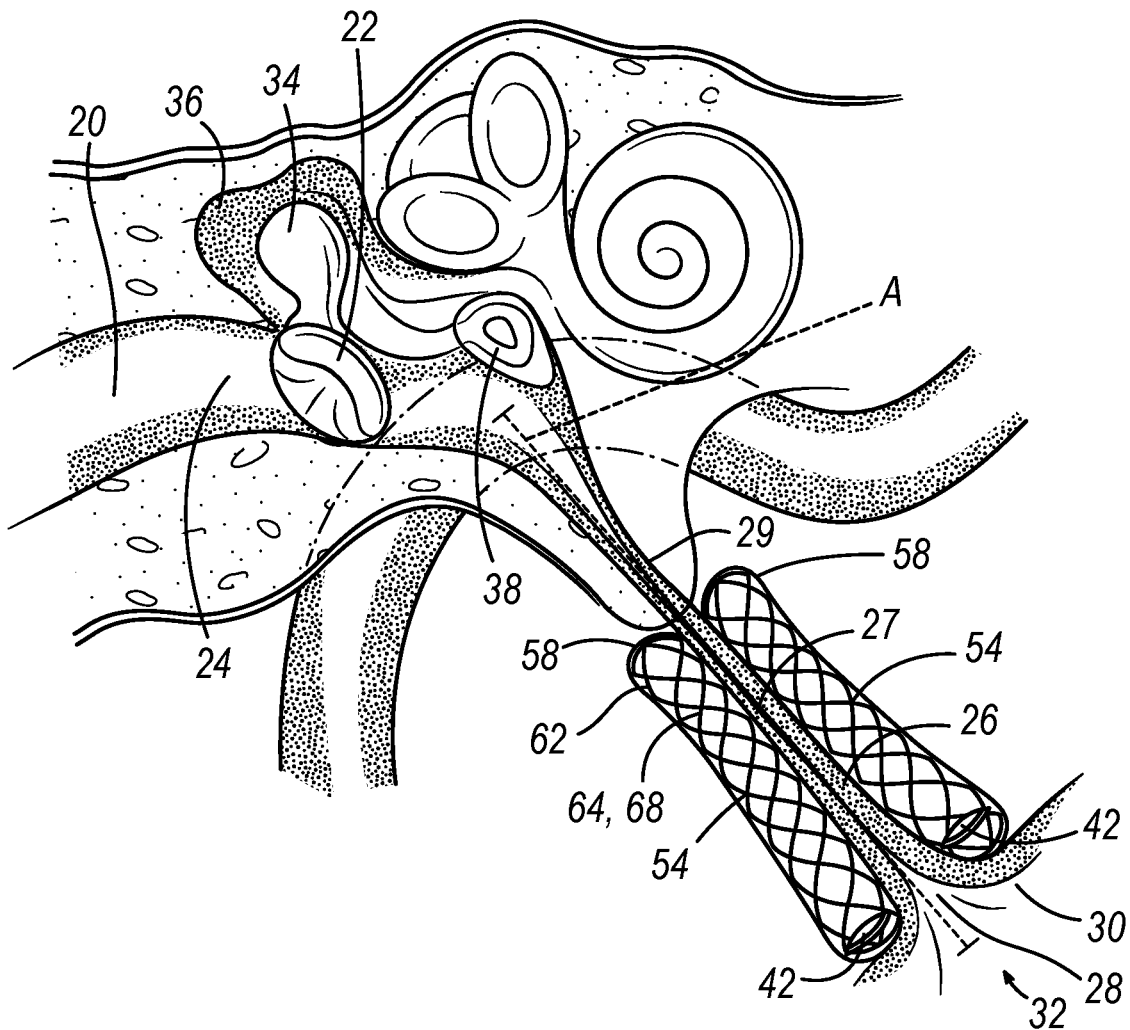
FIG. 18 depicts a cross-sectional view of an ET with two adjacent pockets containing stents in an expanded state to opposingly urge the ET to a closed state.

While the foregoing examples include just one wire structure (52) or just one stent (54) being implanted adjacent to an ET (26), any other suitable number of wire structures (52) or stents (54) may be implanted adjacent to an ET (26). For instance, FIG. 17 shows an example where two wire structures (52) are implanted adjacent to an ET (26). In this example, each wire structure (52) urges a corresponding side of the ET (26) toward the other side of the ET (26), such that wire structures (52) cooperate to opposingly urge the ET (26) toward a closed state. Similarly, FIG. 18 shows an example where two stents (54) are implanted adjacent to an ET (26). In this example, each stent (54) urges a corresponding side of the ET (26) toward the other side of the ET (26), such that stents (54) cooperate to opposingly urge the ET (26) toward a closed state. Any suitable number and combination of wire structures (52) and stents (54) may be utilized to urge the ET (26) toward a closed state. It should be noted that more than two pockets may be used to urge the ET (26) toward a closed state, such as three to six pockets or six to eight pockets. In addition, a single pocket formed around the pharyngeal ostium (28) may also be used to close the ET (26).

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such, at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A method of treating a patulous Eustachian tube, the method comprising: forming a first pocket in a wall of a nasopharynx region proximate to a pharyngeal ostium; inserting a resiliently biased implant within the first pocket; and allowing the implant to expand within the first pocket to thereby urge the Eustachian tube toward a closed state.

Example 2

The method of Example 1 wherein the implant comprises a wire structure.

Example 3

The method of Example 1, wherein the implant comprises a stent.

Example 4

The method of Example 3, wherein the stent comprises nitinol.

Example 5

The method of any one or more of Examples 1 through 4, further comprising inserting an endoscope through a nostril and providing visual guidance of the nasopharynx region with the endoscope.

Example 6

The method of any one or more of Examples 1 through 4, further comprising inserting an endoscope through a patient's mouth and providing visual guidance of the nasopharynx region with the endoscope.

Example 7

The method of any one or more of Examples 1 through 6, further comprising inserting a cutting device through a second nostril and through a nasal cavity to position the cutting device proximate to the pharyngeal ostium, wherein the act of forming the first pocket is performed using the cutting device.

Example 8

The method of any one or more of Examples 1 through 6, further comprising inserting a cutting device through a patient's mouth through the throat to position the cutting device proximate to the pharyngeal ostium, wherein the act of forming the first pocket is performed using the cutting device.

Example 9

The method of any one or more of Examples 1 through 8, wherein the act of forming the first pocket comprises making an incision into the tissue located in the wall of the nasopharynx region proximate to the pharyngeal ostium.

Example 10

The method of any one or more of Examples 1 through 9, further comprising enlarging the formed pocket.

Example 11

The method of any one or more of Examples 1 through 10, the act of enlarging the formed pocket further comprising inserting a shaft into the pocket.

Example 12

The method of any one or more of Examples 1 through 11, wherein a deployment device is used to insert the implant within the first pocket, wherein the deployment device comprises a sheath.

Example 13

The method of Example 12, further comprising retaining the implant within the sheath of the deployment device.

Example 14

The method of Example 13, further comprising retracting the sheath to deploy the implant within the pocket.

Example 15

The method of any one or more of Examples 1 through 14, further comprising supporting the implant with a guide catheter.

Example 16

The method of Example 15 further comprising positioning the implant within the pocket with the guide catheter.

Example 17

The method of any one or more of Examples 12 through 16, further comprising removing the deployment device from the body.

Example 18

The method of any one or more of Examples 1 through 17, further comprising closing the pocket by suturing the incision.

Example 19

The method of any one or more of Examples 1 through 18, further comprising closing the pocket by sealing the incision.

Example 20

The method of any one or more of Examples 1 through 19, further comprising forming a second pocket in the wall of the nasopharynx region proximate to the pharyngeal ostium; inserting a resiliently biased second implant within the second pocket; and allowing the second implant to expand within the second pocket.

Example 21

The method of any one or more of Examples 1 through 20, further comprising inserting into the first pocket a deployment device with a balloon disposed around the guide catheter, wherein the implant is disposed around the balloon; inflating the balloon to thereby expand the implant; deflating the balloon; and removing the balloon from the pocket.

Example 22

A method of treating a patulous Eustachian tube, the method comprising: inserting a wire structure within a pocket, wherein the pocket is located proximate to an opening of the Eustachian tube; and expanding the wire structure within the pocket; wherein the expanded wire structure urges the Eustachian tube toward a closed state.

Example 23

A method of treating a patulous Eustachian tube, the method comprising: inserting a stent within a pocket, wherein the pocket is located proximate to an opening of the Eustachian tube; and expanding the stent within the pocket; wherein the expanded stent urges the Eustachian tube toward a closed state.

III. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, examples, etc. described herein may be combined with any one or more of the other teachings, expressions, examples, etc. that are described herein. The above-described teachings, expressions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK® bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various examples of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of treating a patulous Eustachian tube, the method comprising:
   (a) forming a first pocket in a wall of a nasopharynx region proximate to a pharyngeal ostium;
   (b) inserting a resiliently biased implant within the first pocket; and
   (c) allowing the implant to expand within the first pocket to thereby urge the Eustachian tube toward a closed state.

2. The method of claim 1, wherein the implant comprises a wire structure.

3. The method of claim 1, wherein the implant comprises a stent.

4. The method of claim 1, further comprising:
   (a) inserting an endoscope through a nostril; and
   (b) providing visual guidance of the nasopharynx region with the endoscope.

5. The method of claim 1, further comprising:
   (a) inserting an endoscope through a patient's mouth; and
   (b) providing visual guidance of the nasopharynx region with the endoscope.

6. The method of claim 1, further comprising inserting a cutting device through a nostril and through a nasal cavity to position the cutting device proximate to the pharyngeal ostium, wherein the act of forming the first pocket is performed using the cutting device.

7. The method of claim 1, further comprising inserting a cutting device through a patient's mouth through the throat to position the cutting device proximate to the pharyngeal ostium, wherein the act of forming the first pocket is performed using the cutting device.

8. The method of claim 1, wherein the act of forming the first pocket comprises making an incision into the tissue located in the wall of the nasopharynx region proximate to the pharyngeal ostium.

9. The method of claim 1, further comprising enlarging the formed pocket.

10. The method of claim 1, the act of enlarging the formed pocket further comprising inserting a shaft into the pocket.

11. The method of claim 1, wherein a deployment device is used to insert the implant within the first pocket, wherein the deployment device comprises a sheath.

12. The method of claim 11, further comprising retaining the implant within the sheath of the deployment device.

13. The method of claim 12, further comprising retracting the sheath to deploy the implant within the pocket.

14. The method of claim 1, further comprising supporting the implant with a guide catheter.

15. The method of claim 14, further comprising positioning the implant within the pocket with the guide catheter.

16. The method of claim 1, further comprising closing the pocket by either suturing or sealing the incision.

17. The method of claim 1, further comprising:
   (a) forming a second pocket in the wall of the nasopharynx region proximate to the pharyngeal ostium;
   (b) inserting a resiliently biased second implant within the second pocket; and
   (c) allowing the second implant to expand within the second pocket.

18. The method of claim 1, further comprising:
   (a) inserting into the first pocket a deployment device with a balloon disposed around the guide catheter, wherein the implant is disposed around the balloon;
   (b) inflating the balloon to thereby expand the implant;
   (c) deflating the balloon; and
   (d) removing the balloon from the pocket.

19. A method of treating a patulous Eustachian tube, the method comprising:
   (a) forming a first pocket in a wall of a nasopharynx region proximate to a pharyngeal ostium;
   (b) inserting a wire structure within the pocket; and
   (c) expanding the wire structure within the pocket; wherein the expanded wire structure urges the Eustachian tube toward a closed state.

20. A method of treating a patulous Eustachian tube, the method comprising:
   (a) forming a first pocket in a wall of a nasopharynx region proximate to a pharyngeal ostium;
   (b) inserting a stent within the pocket; and
   (c) expanding the stent within the pocket; wherein the expanded stent urges the Eustachian tube toward a closed state.

* * * * *